US 011798186B2

(12) United States Patent
Barnes (10) Patent No.: US 11,798,186 B2
(45) Date of Patent: Oct. 24, 2023

(54) BODY SHAPE INDICATOR

(71) Applicant: SELECT RESEARCH LIMITED, Malvern (GB)

(72) Inventor: Richard Barnes, Malvern (GB)

(73) Assignee: Select Research Limited, Malvern (GB)

( * ) Notice: Subject to any disclaimer, the term of this patent is extended or adjusted under 35 U.S.C. 154(b) by 0 days.

(21) Appl. No.: 17/042,660

(22) PCT Filed: Mar. 27, 2019

(86) PCT No.: PCT/GB2019/050873
§ 371 (c)(1),
(2) Date: Sep. 28, 2020

(87) PCT Pub. No.: WO2019/186154
PCT Pub. Date: Oct. 3, 2019

(65) Prior Publication Data
US 2021/0065394 A1    Mar. 4, 2021

(30) Foreign Application Priority Data
Mar. 29, 2018    (GB) ..................................... 1805233

(51) Int. Cl.
*G06T 17/00*    (2006.01)
*G06T 7/62*    (2017.01)
(Continued)

(52) U.S. Cl.
CPC .............. *G06T 7/62* (2017.01); *A61B 5/0064* (2013.01); *A61B 5/1077* (2013.01); *G06F 30/20* (2020.01);
(Continued)

(58) Field of Classification Search
CPC ......... G06T 17/20; G06T 19/00; G06T 17/00; G06T 17/10; G06T 17/005
(Continued)

(56) References Cited

U.S. PATENT DOCUMENTS

| 7,242,999 B2 | 7/2007 | Wang |
| 2007/0032898 A1* | 2/2007 | Wang ..................... G06Q 30/06 700/132 |

(Continued)

FOREIGN PATENT DOCUMENTS

| WO | WO 2009090391 A1 | 7/2009 |
| WO | WO 2014183157 A1 | 11/2014 |

OTHER PUBLICATIONS

Ching-Hung Hsu, "Applying a Bust-to-Waist Girth Ratio Approach to Develop Body Measurement Charts for Improving Female Clothing Manufacture", Journal of the Chinese Institute of Industrial Engineers, vol. 25, No. 3, 2008, pp. 215-222, XP055586369, ISSN: 1017-0669, DOI: 10.1080/10170660809509085, abstract, p. 217, right hand column.

*Primary Examiner* — Gordon G Liu
(74) *Attorney, Agent, or Firm* — Patterson Thuente IP (57) ABSTRACT

A body shape indicator device (1) comprises a scanner (2) arranged to obtain a three-dimensional model of a person, a body volume calculator (11) for calculating the volume of at least first, second and third parts of the person's body from the three-dimensional model and a body shape calculator (19) for calculating an indication of the person's body shape based on part volume ratios calculated from the output from at least the body volume calculator. A method for determining the body shape of a person and a method of automated clothing selection based on the body shape as determined are also disclosed.

17 Claims, 5 Drawing Sheets

(51) Int. Cl.
　　　G06T 7/50　　　　(2017.01)
　　　G06F 30/20　　　(2020.01)
　　　A61B 5/00　　　　(2006.01)
　　　A61B 5/107　　　(2006.01)
　　　G06K 19/06　　　(2006.01)
　　　G06Q 30/0601　　(2023.01)

(52) U.S. Cl.
　　　CPC ... *G06K 19/06112* (2013.01); *G06Q 30/0643* (2013.01); *G06T 7/50* (2017.01); *G06T 17/00* (2013.01); *A61B 5/1079* (2013.01); *A61B 2503/12* (2013.01); *G06T 2207/30196* (2013.01)

(58) Field of Classification Search
　　　USPC ......................................................... 345/420
　　　See application file for complete search history.

(56) References Cited

U.S. PATENT DOCUMENTS

| | | | | |
|---|---|---|---|---|
| 2009/0099457 | A1* | 4/2009 | Barnes | G01G 19/50 600/587 |
| 2013/0315475 | A1* | 11/2013 | Song | G06T 7/593 382/154 |
| 2014/0340479 | A1* | 11/2014 | Moore | G06T 17/20 348/43 |
| 2015/0272787 | A1* | 10/2015 | Seitz | A61F 13/47 604/385.01 |

\* cited by examiner

BODY SHAPE INDICATOR

CROSS-REFERENCE TO RELATED APPLICATIONS

This application is filed pursuant to 35 USC 371 as the U.S. national stage filing of PCT Application No. PCT/GB2019/050873 filed Mar. 27, 2019, and claims priority benefits of GB Application No. 1805233.2 filed Mar. 29, 2018.

The invention relates to a device and method for providing an indication of a subject's body shape. More specifically, the invention relates to methods of determining body shape based on body part measurements, and in particular body part volumes. The method disclosed herein is automated, and does not require a human judgement. The device and method disclosed herein may be applicable to the measurement of body shape of persons in all fields, and may find particular utility in the fields of garment and apparel manufacture, design and sizing specification.

Human body measurement has been explored and practised in the academic, ergonomic and scientific fields for hundreds of years. The predominate techniques for measurement have used one- and two-dimensional measurement including tape measures, bespoke manual measurement equipment, and more recently computerised equipment arranged to automatically measure the body to generate automated linear measurements.

Body shape analysis and sizing definition by numeric means originated after the conclusion of the Second World War. Before the war, there was a preference for tailor-made clothes, especially among affluent customers, but the war meant a change in culture and expectations. In terms of clothing, the war meant that made-to-measure clothing was no longer seen as a necessity; universally-produced clothing made to standard sizes was necessary during the war years.

Following the end of the Second World War, a change of culture emerged whereby ease of use and speed of response meant that an acceptance of buying clothes to uniform sizes (which had occurred out of necessity during the war years) gradually became the norm. In 1951, the first 'national' sizing survey was undertaken in the United Kingdom, using manual measurement with funding from the UK Board of Trade. The results were published in the mid 1950's, allowing mass-market retailers to produce size charts as a guide for customers when purchasing clothes.

Tailors who were used to measuring for bespoke clothing had always used specific terms to denote what they believed were descriptive terms of whole 'body shape' so as to record their respective customers' individual requirements. These included terms such as Corpulent, Rotund, Sway Back, and Front Pitch amongst others; some of which are still used by Savile Row tailors today. In the field of ergonomics, the terms most frequently used to describe body shape are Endomorph, Ectomorph and Mesomorph. These are visual descriptors, selected using the experienced and trained human eye.

Body shape definitions provide categories into which individuals' body shapes can be categorised. There may be variation within a category, but the body shape selected provides at least an approximate idea of the individual's shape. Body shapes may therefore be described as body shape categories or types.

After the Second World War, the acceptance by the public of being able to purchase clothing to a standard fit led to industrial development of uniform sizing standards, providing, customers with a more standardised and easy to understand system for buying clothes.

The system of modern sizing developed initially in the 1950's as a result of this change; this permeated through the customer journey and the manufacturing process over the coming decades. The system is further explained in the following two publications about body shape and sizing which helped to form the basis of what is known and accepted as the current system of designating clothes by numeric size, e.g. Size 10, 12, 14 etc.:

Modern Sizing and Pattern Making for Women's and Children's Clothing; Author: Philip Kunick, First published in 1984.

Adultdata: the Handbook of Adult Anthropometric and Strength Measurements: Data for Design Safety (Government consumer safety research) Spiral-bound—1998

Since the mid 1990's there has been a significant development in the field of garment sizing as three-dimensional (3D) measurement of the human body has become available, automatically creating a model of the human body using a combination of sensors and digital cameras to create a digital 3D 'mesh' that is representative of the body of an individual.

Linear or 2-dimensional measurements of the human body, such as waist, hip, leg length, chest girth, arm length etc., can then be extracted from the mesh generated by the 3D measurement technique, which avoids the need for hands-on measurements with tape measures and the likes.

A number of companies produce machinery that is able to produce a 3D image of a human body and extract measurements. These include 3D full body laser and white light scanners by manufacturers such as [TC]2 Labs, Lectra, Telmat, Wicks & Wilson, Human Solutions and Styku, plus other devices such as Kinect®, and smartphone or webcameras or the likes in conjunction with appropriate software, which are used to create a 3D image of a person.

In 2002, results from the "Size UK" UK National Sizing Survey were published, for which the applicant was one of the managing collaborators and the Data Controller for the project under The Data Protection Act (1998). The published results related to the comparative aggregated linear measurements for three key measurements; chest, waist and hips, for both men and women. The aggregated results were presented at a press event held at The London College of Fashion and the data compared from the 2001 sizing survey against the equivalent survey from 1951. High waist girth—a linear measurement—was used to give an indication of body shape.

A review of known techniques for the measurement of body shape in apparel, published in 2006, is "Analysis of Body Measurement Systems or Apparel" by Elizabeth Bye et al. Various options for the measurement of the body for clothing are discussed, including measurements of body 'shape', using various combinations of linear measurements. For women, body shape classifications are mainly based on the circumference of the bust, waist, and hip (BWH), e.g. 91-61-91 cm (36-24-36 inches). For the BWH values listed, the waist-hip ratio is 24/36.

According to a first aspect of the invention, there is provided a body shape indicator device comprising:
a body volume calculator arranged to:
receive a three-dimensional (3D) model of a person generated using a scanner; and
calculate the volume of at least first and second parts of the person's body from the 3D model.

The body shape indicator device may further comprise a body shape calculator arranged to calculate an indication of the person's body shape based on one or more ratios between volumes of the first and second parts. The body shape indication is an indication of a body type may be selected from a predefined list of body shapes. The volumes of the first and second parts may each be thought of as part volumes.

The body shape indicator device may be a clothing/garment selection tool. The body shape indication may provide an indication as to clothing fit.

Figure 2A:
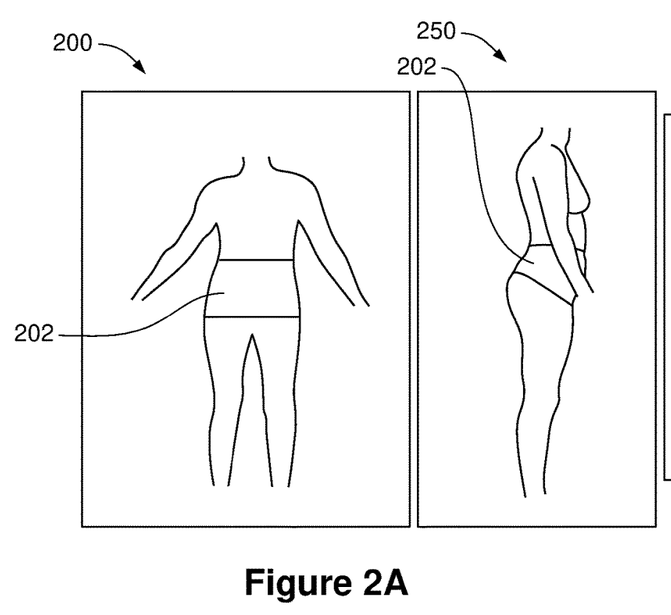
FIG. 2A shows example front and side body shape scans obtainable by a body shape indicator device for a single subject.
Figure 2B:
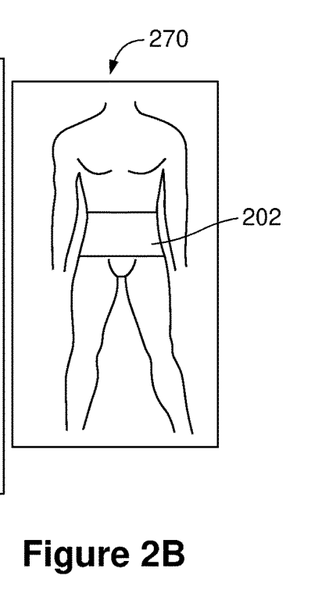
FIG. 2B shows an example front body shape scan obtainable by a body shape indicator device for a single subject.

It will be appreciated that the 3D model of a human body can be segmented into multiple parts for the sake of calculations, each part having a volume. Each volume of a part may be referred to as a part volume. The segmentation may be performed in many different ways, for example by splitting body parts (e.g. each arm, or the torso) using planes (which may or may not be horizontal and/or vertical, as shown in FIGS. 2A and 2B), or by defining edges of a part e.g. by image recognition (for example using image recognition to identify lines of clothing and setting or adjusting the segmentation accordingly—a part may therefore have curved edges as well as or instead of straight edges generated by the intersection of a plane with the body model).

Body shape can therefore be classified and measured using three-dimensional body volume. This is in contrast to the existing prior art of visual interpretation (human eye), two-dimensional measurement using a whole-body linear outline (a drawing), or two-dimensional measurement using linear techniques, whether undertaken using a tape measure (manual) or a three-dimensional body scanner process (automatic).

The scanner may be referred to as a body scanner. As used herein, a "body scanner" or scanner is any device and/or software which can be used to create a three-dimensional model of a person.

This is advantageous as the three-dimensional (3D) model is used to calculate the indication of a person's body shape; the use of volume ratios takes into account the unique build and body shape of an individual person. An accurate indication of the person's shape can be calculated which can be used to accurately select tailored clothing, looseness/snug fit characteristics and/or general style considerations for each customer. Further, ergonomic considerations based on body shape could be used in the design process for children's play areas or toys, and/or furniture and accessories. This use of part volumes, and therefore weight distribution, in the measurement of body shape allows whole body shape to be used in the clothes manufacturing process in a considered and structured measurement process.

The body shape indicator device may therefore be used as a tool in the selection of clothing or the likes.

Further, in an automated selection device or method (e.g. for clothing), machine learning may be used to 'learn' customer preferences and likes/dislikes, so further improving the relevance of suggestions beyond mere physical fit.

The device of the invention may be easy to use, non-invasive, subject friendly and completely safe by using non-penetrating radiation imaging techniques, while being accurate and providing a reliable indicator of a person's body shape.

It is understood that, to the trained human eye, a person can be defined as being 'pear-shaped' or 'apple-shaped', for example, so identifying a body shape for that person. Being pear-shaped or apple-shaped is effectively a generic description for different weight distribution of people. It has been found that using the output from the body shape calculator (which may be a separate entity in its own right—a body shape calculating device or may be provided by a part of another device—e.g. a software module loaded within the smartphone or other computer, which may or may not also be the scanner) an accurate indication of a person's body shape may be obtained without requiring a trained observer.

The invention comprises a novel method of defining human body shape, using part-volumes of the human body to determine an indication of body shape (e.g. apple-shaped, pear-shaped, athletic-shaped, stick thin, hourglass-shaped etc., plus any other permutations of body shape suitably defined in terms of part volume ratios).

Prior art definitions of body shape are descriptive terms of the whole body shape only with no use made of part body volume measurements. The inventor appreciated that part body volume ratios provide a novel and appropriate means of defining and assigning body shape categorisation. By contrast, in the prior art, measurements extracted in the retail clothing field are linear measurements for clothing design, with the exception of single part volume being used for specific clothing designs, such as measuring bust volume specifically for bra fit and breast surgery.

Using multiple part volumes of the person's body has been found to be accurate as it takes account of body shape and body mass distribution that cannot easily be realised by making 1D or 2D measurements such as waist, chest, bust and hip measurements as in prior art methods. This may be especially effective if the body part volumes used comprise the volume of the abdominal region. One of the volumes used may be total body volume.

The body shape calculator may calculate the indication of a person's body shape based on the ratio between the volume of the first part and the volume of the second part, and optionally also the ratio between the volume of the first and/or second part and the volume of any further parts. Thus, by comparing the volume of various body parts the shape of a person can be recognised by measuring the weight distribution.

In some embodiments, 3, 4, 5, 6, 7 or more part volumes may be used in a single ratio, or in a plurality of ratios.

Each part volume may have at least one dimension of over 10 cm, over 20 cm, or over 30 cm.

Typical ratios may include pelvis or chest volume to whole body volume, chest volume to abdominal volume, abdominal volume to pelvis volume, or abdominal volume to whole body volume or a combination of these ratios.

Preferably, the body volume calculator additionally determines the volume of one or more of third, fourth, fifth, sixth, seventh body parts and the shape calculator calculates ratios between the volumes of these parts to obtain the indication of a person's body shape.

The shape calculator may use further data such as gender, age, perceived dress or clothing size, and/or ethnicity.

Preferably, the body volume calculator calculates the volume of predetermined parts of the person's body, which are used by the shape calculator to calculate the indication of the person's shape.

The body shape calculator and body volume calculator may be provided by the same device and/or software, or may be separate.

Preferably, the predetermined parts are associated with an importance factor, which is used to give more importance to particular parts of the body in the calculation of the person's shape. Thus, the indication of a person's shape can take account of particular areas of the body where marked differences would be expected for different body shapes. The chest and/or abdomen part volumes may be given a higher importance factor as compared to other part volumes.

In some embodiments, the shape calculator calculates the volume of the abdominal region as the first part, the volume of the upper torso (chest) as the second part and the volume of the lower torso (pelvis) as a third part. Preferably, the volume of the first part is compared to the volume of the second and third parts and the indication of body shape determined therefrom. It will be appreciated that other part body volumes may be used, for example where excessive limb volume may be a factor. For example, people of extreme athletic build, such as bodybuilders may have excess arm volume, and those of higher lower body volume, such as afro-Caribbean females may have additional leg volume.

By determining the indication of a person's shape in this way a differential anthropometric measure is created that takes account of differing torso shapes and differing whole body shapes, based upon which parts of a person's body have more volume, and therefore weight, associated with them.

The scanner used to generate the 3D model, which may or may not be a part of the body shape indicator device, may be of a known type and may be a body scanner such as an on-line 'cloud-based' 3D scanner, or a white light or laser 3D scanner. The data capture process, and optionally the scanner, may, alternatively or additionally, be provided by a smartphone or the likes with appropriate software, e.g. an app. The generation of the 3D model may be performed separately from the data capture process.

Data capture processes which are passive, such as photography, rather than actively emitting radiation, may be advantageous as they do not subject the person to a dose of ionising radiation like certain known scanning techniques, nor to flashes of light, which may have a negative effect on epileptic users for example.

In summary, such a scanner may take many measurements, known as data points, for example hundreds, thousands, or millions of measurements on the surface of a person's body (typically 100 to 130 million data points for white light scanners). These data points can then be appropriately joined or associated with neighbouring points to form a three-dimensional image of a person.

It will be appreciated that other scanners capable of taking the appropriate measurements to generate the 3D model may also be used, including a Kinect® devices, and/or smartphones. The data processing and calculation of a body shape indication may be performed by a processing means of the scanner, or by a separate module or device.

In additional or alternative embodiments, a 3D scanner may be or comprise a processing device or module, which may be implemented as software, arranged to produce a 3D model of a person using outlines created from 2D digital images of a person; for example just two images—one front and one side. Such a 3D scanner may exist solely on a 'cloud' server. The skilled person will appreciate that any suitable process, currently known or developed in future, may be used to generate the 3D model and extract the part body volumes.

The body shape indicator device may store the 3D model and the indication of a person's shape. The shape indicator device may determine whether the person being scanned has been scanned previously and, if so, show at least a comparison between the present 3D model and the previous 3D model.

Irrespective of the scanner used, a 3D model of a person is produced by one or more devices. This model may then be used for part body volume analysis to determine an indication of body shape. The scanning and generation of the model may be performed by a device/as part of a method of various embodiments, or may be generated separately, optionally with one or more different devices, for use in other embodiments.

The body shape indicator device may be used to collect body shape information statistics, which may be stored in a database. The database may be arranged to be accessed from a secure web server. The statistics may be accessible only by the person scanned, or may be made available to retailers and/or manufacturers, for example. The statistics may be used to guide clothing range development.

The body shape indicator device may be arranged to calculate the volume of a third part of the person's body from the 3D model. The body shape calculator may be arranged to calculate the indication of the person's body shape based on one or more ratios between volumes of the first, second and/or third parts.

One of the first, second and third parts may be total body volume.

The body shape indicator device may further comprise the scanner. The scanner may be arranged to scan the person's body. Alternatively or additionally, the scanner may receive scan data generated by one or more other devices for processing.

The scanner may obtain scan data and generate the 3D model of the person from the scan data. The scanner may generate the scan data, or may obtain the data to be used to generate the 3D model from another source.

The first and second parts may comprise first and second parts of the person's torso; the torso may be sub-divided into a plurality of parts.

The first and second parts may be:
(i) two of: chest, abdomen and pelvis; or
(ii) torso below the waist and torso above the waist.

The body volume calculator may be arranged to calculate the volume of further predetermined parts of the person's body, which may be used by the body shape calculator to calculate the indication of the person's body shape. One or more linear or area measurements, such as waist circumference or cross-sectional area, may also be used.

The device may be arranged to associate the first, second, and any further predetermined parts with an importance factor. The importance factor may be used to give more importance to particular parts of the body in the calculation of the indication of the person's body shape.

The device may be arranged to calculate the volume of a total of three body parts, the three body parts being chest, pelvis and abdomen.

The device may be arranaed to calculate the volume of a total of seven body parts, the seven body parts being left arm, right arm, left leg, right leg, chest, abdomen, and pelvis.

The body volume calculator may be arranged to manipulate the data output from the scanner using triple integration.

The body shape indicator device may be arranged to calculate linear measurements from the 3D model and to provide an indication of a suitable clothing sizing fit based at least in part on the body shape indication and the linear measurements.

The body shape indicator device may be arranged to provide a graphic code encoding at least one of the indication of the person's body shape and measurements (e.g. volumetric and/or linear measurements) of the person.

According to a second aspect of the invention, there is provided a method for determining the body shape of a person. The method may comprise the steps of:

obtaining a three-dimensional (3D) model of the person's body generated using a scanner;

calculating the volume of a first part of the person's body from the 3D model;

calculating the volume of a second part of the person's body from the 3D model; and calculating an indication of the body shape of the person from one or more ratios between the volumes of the first and second parts, wherein the body shape indication is an indication of a body type selected from a predefined list of body shapes.

The method may further comprise scanning the person's body using the scanner, and/or receiving 3D or 2D scan or image data of the person at the scanner.

The method may further comprise generating the 3D model of the person's body.

The method may further comprise generating and providing a graphic code arranged to encode or provide access to the body shape indication.

The indication of shape may be obtained quickly, easily and accurately by the above method. As a scanner is used, the data collected is a true and undistorted representation of a person's size and shape. The calculation of a person's volume or, in particular, the part volumes of predetermined body parts, using a scanner may give an accurate representation of a person's volume without the need to submerge them in an underwater weighing tank in water, for example.

Preferably, the indication of the person's body shape is calculated using a ratio between the first volume and the second volume. As discussed in relation to the first aspect of the invention, the volume of various first and second body parts may be chosen. However, the first and second body parts preferably comprise the abdominal area and the upper torso (chest).

Preferably, the volume of further predetermined parts of the person's body are calculated and used in the calculation of the indication of the person's shape.

According to a third aspect of the invention, there is provided a method of automated clothing selection. The method may comprise the steps of;

obtaining a three-dimensional (3D) model of the person's body generated using a scanner;

calculating the volume of a first part, and a second part of the person's body from the 3D model;

calculating an indication of the body shape of the person from one or more ratios between volumes of the first and second parts, wherein the body shape indication is an indication of a body type selected from a predefined list of body shapes; and selecting a clothing style or fit based at least in part on the body shape indication.

The method may further comprise scanning the person's body using the scanner, and/or receiving 3D or 2D scan or image data of the person at the scanner.

The method may further comprise generating the 3D model of the person's body.

Further, use of a scanner may be less invasive than having another person make numerous "hands-on" measurements and there may be no intervention. Still further, manually measuring someone can lead to inaccuracies due to how tight the measuring tape is held, which can, for example, compress soft areas leading to an inaccurate, reduced, measurement. This problem is common as often the measuring tape bridges the small of the back between body mass either side of the spine. Thus, the person may be more relaxed due to the absence of physical contact and the data collected is more accurate and also more detailed.

According to a fourth aspect of the invention there is provided a machine readable medium containing instructions to allow any of the above methods to be provided.

According to a fifth aspect of the invention there is provided a machine readable medium containing instructions to cause any of the above apparatus to function.

The machine readable medium according to any of the above aspects of the invention may comprise any of the following: a floppy disk, a CDROM/RAM, a DVD ROM/RAM (including −R/−RW and +R/+RW), a Blu ray disc, an HD DVD, a memory (including a Memory Stick, SD card, Flash memory card or the like), a hard drive, a cloud server, a digital camera, an I-Drive, any form of magneto optical storage, a transmitted signal (including an Internet download, an FTP transfer or the like), a wire.

In summary, embodiments of the invention may serve to integrate an indication of a person's body shape into the apparel and clothing industry as a new parameter of measurement; using part body volume to determine the body shape of a person.

The current, prior art, system relies upon a numeric sizing system (e.g. Size 10, 12, 14 etc.) as a guide for the public when choosing and selecting the best fit, which does not account for weight distribution variations within a weight category. Embodiments of the invention are therefore intended to provide the clothing purchaser with a 'copy' of their body shape, which may be obtained through delivery of their volumetric (and optionally linear measurements) through a QR code or similar technical means. This may allow the clothing buyer to have a shape 'passport' whereby they can submit their shape to a specific retailer, allowing direct comparison to the manufacturing specification as implemented by that retailer. The graphic code may be available for use via an Application Programming Interface for and in a retail environment on-line, in-store or at home.

The body shape of the customer is likely to remain consistent at any given time, allowing each retailer to allow a customer to directly compare their body shape to the range of manufactured garments, so as to find the best fit at that time. An Application Programming Interface (API) may be used for the comparison. If the body shape of the customer changes over time, then a re-scan using the 3D scanner may allow the clothing customer to obtain a new 'passport' with which to shop on-line or in store.

Embodiments of the invention may also be implemented in the apparel design and manufacturing process, integrating body shape for the first time as an additional element of body measurement. This may allow better fit of clothing in the future by placing the onus of responsibility on the customer to use their body shape when purchasing clothing. This may alleviate the current reliance upon the single number, produced by mass market retailers, as an indication of size, which may or may not be appropriate to people of the same perceived size, but who have different body volume distributions.

The skilled person will appreciate that features described with respect to one aspect may be applied to any other aspect, *mutatis mutandis*. Further, features and/or aspects of the invention may be provided as software, firmware, and/or hardware.

There now follows by way of example only a detailed description of embodiments of the present invention with reference to the accompanying drawings in which.

The embodiments described herein relate to a body shape indicator device that can be used to at least partially automate clothing selection, design or tailoring and/or to improve the online clothing sales experience by reducing the risk of a purchased garment not fitting by the integration of body shape definitions into the process. The skilled person will appreciate that the body shape indication may have uses outside of clothing; for example assisting with the selection of an appropriate prosthetic, mobility aid, seating design, ergonomic tools or the likes.

Those working in the field of the art will appreciate that body shapes vary significantly—even for two people of the same general clothing size and/or weight, weight can be differently distributed and bone structures may vary. As such, a numeric clothing designation is insufficient to determine whether or not an item of clothing will fit. For example, in women, chest/bust size in particular can vary significantly and have a marked effect on how clothing fits.

Whilst someone working in the field, for example a clothing retail assistant, tailor, or seamstress, may be easily able to identify another person's body shape by eye, an individual may not be able to do so for him or herself. An automated method of body shape designation, not requiring a trained person, may therefore be beneficial.

Figure 1A:
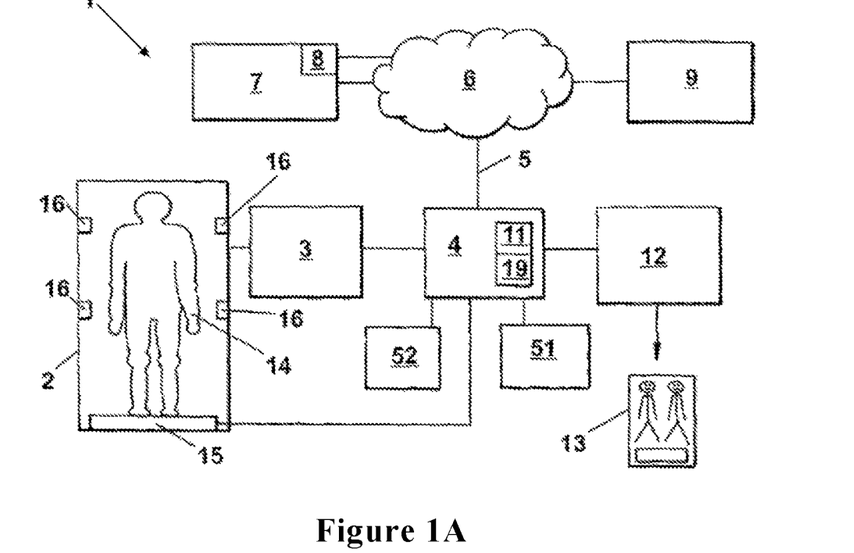
FIG. 1A shows a diagrammatic representation of the body shape indicator device.

In FIG. 1, a body shape indicator device 1 is shown comprising a scanner 2 and data collection means 3 and a data processing and user interface means 4. The scanner 2 may be separate and not a part of the body shape indicator device 1 in other embodiments—in such embodiments, the body shape indicator device 1 obtains data from a scanner 2, directly or indirectly.

In the embodiment shown, the data processing and user interface means 4 has a connection 5 to the Internet 6 so that it can communicate with a remote server 7. It will be appreciated that the connection need not be via the Internet 6 (or other Wide Access Network) and may be over a Local Area Network, a direct connection or over a telephone line depending upon the location of the user interface terminal 4 and the remote server 7. In still further embodiments, there may be no remote connection or communication.

In the embodiment being described, the remote server 7 comprises a list of body shape definitions; a corresponding body shape from this pre-defined list is selected when a user 14 is scanned.

In the embodiment being described, the remote server 7 comprises clothing information; appropriate clothing for the user 14 may be selected based at least in part on the determined body shape. The user 14 may browse recommended clothing, and/or place an order, via the user interface means 4. Advantageously, storing body part definitions on the remote server 7 may allow these to be updated centrally by a clothing provider.

In other embodiments, the device 1 may not have an internet connection or equivalent. Instead, the user interface terminal 4 may provide the indication of body shape to the user 14 (and/or to another person such as a store assistant), and the user 14 may use that indication to guide clothing purchase decisions or the likes. In such embodiments, the body part definitions may be stored locally, for example by the data processing and user interface means 4.

In the embodiment being described, the body scanner 2 comprises a bi-plane imaging technique whereby two (or more) digital images are processed into outlines of the user 14 and then processed through a server to match to known and verified outlines of three-dimensional data models. The outlines are used to generate a 3D model of the user 14.

'Machine Learning' and/or various bespoke algorithms may be used to convert and match the known outlines and analyse the variances to create a new 3D model that best matches the user 14.

This 3D model may then be used to extract linear and volumetric measurements, including part body volumes used to assess and classify body shape. Measurements of the size and shape of the user 14 may therefore be obtained from the 3D model.

The digital images may be photographs. The scanner 2 may obtain the measurements, or the 3D model may be passed to another device or module for processing.

The data collection means 3 comprises software loaded onto a computer that is connected to, or integral with, the scanner 2. The data processing and user interface means 4 comprises software loaded on to the same computer in the embodiment shown, wherein the software receives its input from the output of the scanner software 3. The data manipulation software 4 includes a body volume calculator 11 and a body shape indicator module 19, both embodied as software in the embodiment being described. The skilled person will appreciate that some or all of the software 3, 4 could be replaced with hardware in some embodiments.

The data processing and user interface means 4 passes the data from the data collection means 3 to the body volume calculator 11 with any additional information as appropriate. For example, the data processing and user interface means 4 may specify for which body parts the volume calculator 11 should calculate volume.

In the embodiment being described, the data processing and user interface means 4 allows a user 14 (or other person) to enter further information such as gender, age, type of clothing sought, and if any particular body part should not be measured (e.g. due to a plaster cast or injury making it likely that such a measurement would skew the result). The selection of body parts for which the volume calculator 11 should calculate volume may be influenced by the data provided—for example choosing different body parts for children (early years and/or teenage) as compared to adults, and/or for men as compared to women.

The output from the body volume calculator 11, and optionally any further information, is passed to the body shape indicator calculating module 19. The module 19 calculates a ratio between the first volume, corresponding to the first body part output by the volume calculator, and the second volume corresponding to the second body part output by the volume calculator. The module 19 may calculate a ratio between the first volume and/or the second volume, and the third volume corresponding to the third body part output by the volume calculator, and/or any further volumes calculated.

In some embodiments, the further information provided may be used to determine which body parts to measure, which ratios to use, and/or which predefined list of body shapes to use. The selection of which predefined list of body shapes to use may vary depending on the intended use of the body shape indication—for example choosing a different list if the indication is wanted for ergonomic or research purposes instead of clothing purposes, or depending on the clothing brand of interest.

The connection 5 may also be used to update the data manipulation software 4 from a computer server (not shown) also connected to the Internet.

In the embodiment shown, the data processing and user interface means 4 is connected to an output means 12, which comprises a printer in the embodiment being described. The printer 12 is able to print a datasheet 13 showing at least the output from the data processing and user interface means 4. The output may include one or more of:
(i) a body shape indication;
(ii) pictures of the 3D model generated;
(iii) clothing recommendations (e.g. hyperlinks, item codes, words and or images).

In alternative or additional embodiments, the output means 12 may comprise a graphic code generator. The output means 12 may generate a QR code or the likes, the QR code doing either or both of encoding body shape information of the user or identifying the user's account or details such that the body shape information for the user can be looked up in and retrieved from a database using the QR code.

The QR code (or other output) may then be used, for example via an Application Programming Interface (API), to allow a customer to compare their body shape to a range of manufactured garments for a certain retailer, so as to find the best fit within that retailer's products, irrespective of the designated size 'number' for each garment.

In the world of sizing and fit, up to 40% of clothing is returned due to incorrect sizing or fit, so retailers suffer economic loss and customers have a poor retail experience—the current sizing system is not sufficient to provide a reliable fit. Embodiments of the invention rely on part-volumes of the body enabling a person's body dimensions to be determined in 3D to provide new criteria and a new definition of human body shape. This new measurement parameter based on part volume distribution allows garment specifications, through an Application Programming Interface (API) or the likes, to be linked directly through a 'QR Code' to the individual body shape of customers using the technology.

In some embodiments, a bespoke machine learning system may be used to process the data, for example live/in real time. Such a system can, over time, learn about the specific choices of the customer, such as style, looseness or tight fit and colour, to provide predictive learning on garment choice based on their individual body shape. This may also allow a retailer to send notifications or marketing information about garments that will be the best fit for that customer based on their body shape incorporating all of the subjective criteria that an individual may prefer; which are learnt over time by the machine learning algorithms on body shape volumes.

Instead of relying on the 'best guess' of which arbitrary number (e.g. Size 12) might fit, the user 14 may use their shape 'passport' to shop in store or on line, with the machine learning (through an API) optionally providing further refinements in some embodiments, linking through to the retailer garment specifications that are used to specify the garment manufacture.

Machine learning applications can be applied to collect, process analyse big data turn to NoSQL databases as well as Hadoop and its companion tools, including: YARN, MapReduce, Spark, HBase, Hive, Kafka, Pig. In some cases, Hadoop clusters and NoSQL systems may be used primarily as landing pads and staging areas for data before it gets loaded into a data warehouse or analytical database for analysis, usually in a summarised form that is more conducive to relational structures. Data may be analysed directly in a Hadoop cluster or run through a processing engine like Spark. For both ETL and analytics applications, queries may be written in batch-mode MapReduce; programming languages, such as R, Python and Scala; and SQL, the standard language for relational databases that's supported via SQL-on-Hadoop technologies. Such techniques may be used to create a system to handle individual body shape type analysis based on partial body volumes of different people. In embodiments in which it is used, the machine learning may provide further refinements such as fit preference ranges within a body shape or the likes. Various embodiments may therefore be used to identify different levels or extents of a particular body shape—e.g. how hourglass shaped someone is—or indeed to identify new body shapes.

Figure 1B:
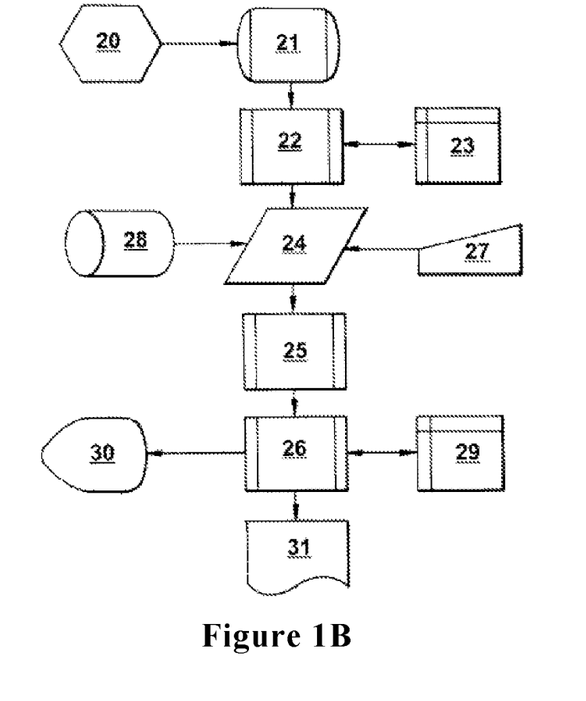
FIG. 1B shows a diagrammatic representation of a method of using the body shape indicator device.

FIG. 1B shows a flow chart of the scanning method. In use, an operator might oversee the scanning process, or a user may operate the device 1 him- or herself.

The operator would brief a person 14 (shown in FIG. 1) to be scanned on the scanning process including what posture to adopt and how to initiate the scanning process. In embodiments without an operator, written and/or visual instructions may be provided.

The person 14 would generally undress to underwear (or close-fitting garments) in a changing booth adjacent to, or containing, the scanner 2. These steps are represented by numeral 20. The person 14 is scanned at 21, which involves entering the scanner 2, adopting the predetermined position and initiating the scanning process.

The scanners 2 used by embodiments of the present invention are known and will not be described in detail, as the skilled person will appreciate that any suitable scanner may be used, and that many embodiments take a pre-generated 3D model and therefore may not involve or require a scanner.

One or more cameras 16 are used to obtain images of the user 14, from which outlines of the user's body can be extracted.

The scanner 2 then processes these outlines to generate a "3D cloud" of data points that is processed by the data collection means 3 at step 22 to generate a "wire-frame" 3D model of the person 14. The raw or model data is stored 23 in storage means (not shown). The stored data can be recalled from the storage means as required. The storage means may comprise memory, a hard disk and optical media or may be a remote device connected to the data collection means 3 by communication means. The data collection means 3 may also make simple calculations on the model data such as the height of the person 14. Therefore, the model data and the calculations are received by the software 4, which may be referred to as manipulation software 4.

The data from the data collection means 3 is output to the manipulation software 4. Steps 24 and 25 represent part of the method performed by the manipulation software 4. The data manipulation software 4 is adapted to receive additional information at step 24 about, and/or input by, the person 14 being scanned.

This additional information may be received automatically, for example from a user's account, and/or may be inputted manually 27. The information received automatically may be retrieved from local memory, or obtained via a dedicated device interface or a serial connection, for example. It will be appreciated that any appropriate means for receiving the information may be employed.

Step 25 represents at least the actions performed by the body volume calculator 11 and the body shape indication determining module 19. The body volume calculator 11 modifies the 3D model data and applies a triple integration to calculate the volume. It will be appreciated that any appropriate method may be used by the volume calculator 11 to calculate the volume of the first body part and the second body part and any further body parts. The first, second and any further volumes calculated from the model therefore correspond to the volume of the person 14 or part volumes thereof.

At step 25 the body volume calculator 11 uses the model data output by the data collection means 3 to identify and calculate the volume of parts of the model that correspond to predetermined parts of the person's body 14. The volume calculator 11 calculates at least the volume of a first part, such as the mid-section around the stomach, a second part, such as the pelvis, and optionally a third part, such as the chest or total body volume. The parts chosen may vary depending upon the person's gender or other parameter, or the clothing type sought, etc. Volume in the context of a part volume of the body constitutes a description of the partial weight of that part of the body—body shape is in essence a description of the whole, but can be defined, using embodiments of the invention, by the measurement of weight distribution.

The volumes of the various parts of the model calculated by the body volume calculator 11 are passed to the body shape determining module 19.

The body shape determining module 19 then calculates an indication of the person's 14 body shape using at a ratio between the first and second part volumes, and optionally one or more further ratios involving third or further volumes of other parts of the body. An importance factor may be applied to one or more of the body volumes, and/or to one or more of the ratios, to change weightings in the body part determination. One of the part volumes may be the whole body volume in some embodiments.

It will be appreciated that the data manipulation software 4 and volume calculator 11 can be programmed to calculate the appropriate volume or volumes depending on parameters such as the person's age or gender, or the application of the device 1 (e.g. the type of clothing or ergonomic tool sought).

In addition, absolute measurements (as opposed to ratios) may be determined and used to provide an indication of appropriate clothing sizes. Due to differences in fit, the skilled person will appreciate that a size 12 garment from one manufacturer and a size 10 garment from a different manufacturer may be the best fits for a particular individual, due to different designs or cuts by each manufacturer. To provide a true fit for an individual, clothing size information designed for mass-market production may therefore need be more detailed than the currently-used single numerical output.

Once the data manipulation software 4 has performed its manipulation 25 of the data output from the data collection software 3, a record may be created of the person's scan and/or the statistics calculated by the data manipulation software 4 and/or the body shape indication. If the person 14 has been scanned previously (e.g. already having a user account with scan data), the model data and other information may be used to replace older data in the previously created record at step 26. The record is also stored 29 and displayed to the person and/or operator on a display means (not shown) at step 30. In other embodiments, data may be deleted once a user or operator has been informed of the body shape indication.

In the embodiment shown, a datasheet 13 is printed at step 31 by the output means 12. The datasheet 13 may include the body shape indication, one or more recommended clothing sizes (e.g. listing a different clothing size for each of three different manufacturers), and/or one or more recommendations of particular styles or items of clothing that would be expected to fit the indicated body shape of the individual well. Further information such as the name (or a username) of the user 14 and/or one or more personalised discount codes or other offers may also be provided. In alternative or additional embodiments, the same or different information may be encoded in a graphic code, such as a QR code, which is provided to the user. The skilled person will appreciate that any graphic code currently known or developed in future, or any future equivalent, may be used, and that this may be provided digitally (e.g. via email, Bluetooth® or the likes) and/or in a form that can be scanned, such as printed on a voucher or loyalty card.

In alternative embodiments, no data may be printed and/or no data may be stored. The device 1 may instead be used to temporarily provide a body shape indication and any other information (e.g. displayed on a screen) and then to wipe all data relating to that user after a set period and/or as soon as the output is acknowledged (e.g. by a user clicking a button labelled "OK", "Finished" or the likes).

In some embodiments, a user 14 may be provided with a graphic code, such as a QR code, encoding or providing access to the user's data.

In such embodiments, once the data has been collected, body shape information (e.g. the body shape indication, volume measurements, and/or linear measurements) of the user may be stored in a QR code which is provided to the user 14. The body shape information may then be accessible by the user online, for example using a smart phone, or via a loyalty card. In embodiments in which multiple part volumes are stored, instead of simply the calculated body shape indication, when the QR code is read by another device and/or code of a website or the likes, that device or website may use the measurements to determine a different body shape indication (e.g. from a different list, specific to a retailer associated with that device or website). The QR code may therefore act as a tool for body shape identification, which may be used by the individual across different manufacturers and retailers, reducing or avoiding the need for further scans or other measurements.

FIG. 2A illustrates front 200 and side 250 scans of a user 14, with the abdomen region 202 highlighted for reference. FIG. 2B illustrates a front scan 270 of a male user, with the abdomen region 202 highlighted. The skilled person will appreciate that one or more ratios involving abdomen volume, e.g. (abdomen volume):(total volume) and/or (abdomen volume):(chest volume) and/or (chest volume):(abdomen volume+pelvis volume) may be important in determining body shape in various embodiments.

Figure 2C:
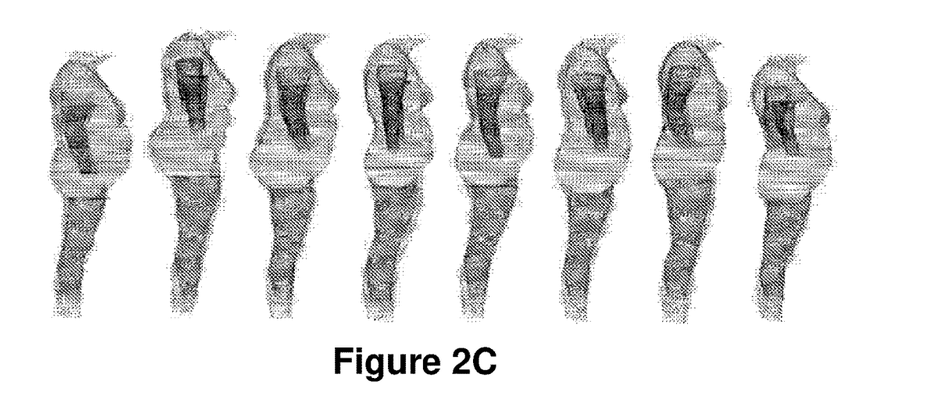
FIG. 2C shows example side body shape scans obtainable by a body shape indicator device for eight women with a Body Mass Index (BMI) reading of 30, illustrating differences in weight distribution.

FIG. 2C illustrates side scans of eight different women, all with a body mass index (BMI) of 30, which is generally equated to size 16 (UK retail sizing). As can be seen from FIG. 2C, despite having the same BMI (30) and retail clothes size (16), these women have a variety of different body shapes. Taking into account body shape in the clothing selection/buying process may facilitate obtaining better-fitting clothing.

Some commonly-accepted body shapes are as pear, apple, hourglass, and stick thin. Various classifications are used to describe body shape types, for example:

- V-shape: proportionally smaller buttocks, bigger chests and wider shoulders, and a small waist, making the torso V-shaped. This body shape is more common in men than women.
- Apple: stomach region wider than the hip section. This body shape is more common in men than women.
- Rectangle/straight/banana: hip, waist, and shoulder regions are of relatively similar width.
- Hourglass shape: narrower waist in both front and profile views. The breasts and buttocks make the chest region and hip region, respectively, broader than the waist, resulting in an hourglass shape. This body shape is more common in women than men.
- Pear/spoon/bell: hip section wider than the upper body. This body shape is more common in women than men.

In the UK, the following twelve body shape definitions are commonly used in the art:

Group 1 Body Shapes—Broad Shoulders, No Defined Waist

Figure 3A:
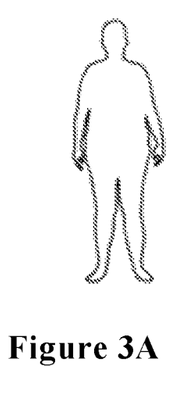
FIGS. 3A to 3L illustrate the twelve body shapes generally defined and used in the art in the UK.
Figure 3B:
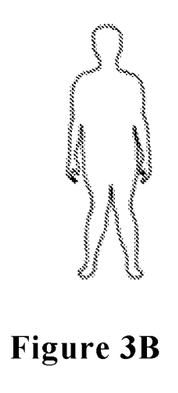
Figure 3C:
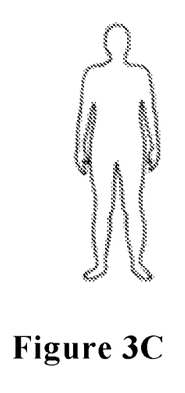

Apple (FIG. 3A)
Characterised by the tummy being the largest part, and a generally rounded and soft shape.
Brick (FIG. 3B)
Characterised by squareness and lack of curves.
Goblet (FIG. 3C)
Characterised by broad shoulders, no defined waist (remainder of group not falling into Apple or Brick definitions).

Group 2 Body Shapes—Chest/Breasts and Hips Similar Size

Figure 3D:
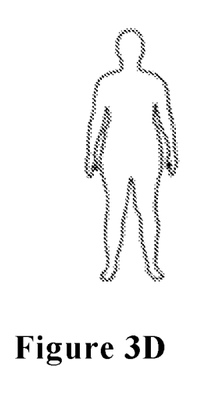
Figure 3E:
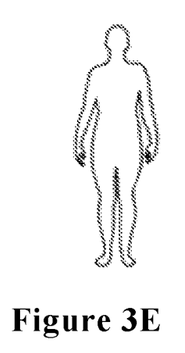
Figure 3F:
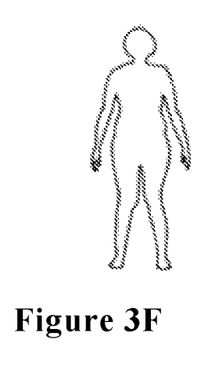

Hourglass (FIG. 3D)
Feminine curves, with generous bosom and hips and a small waist, give the classic hourglass figure.
Vase (FIG. 3E)
Vases are basically stretched hourglasses; equivalent curves but on a generally taller frame.
Cello (FIG. 3F)
Broad shoulders like the Goblet, but with a more curvy waist.

Group 3 Body Shapes—Hips Wider Than Shoulders

Figure 3G:
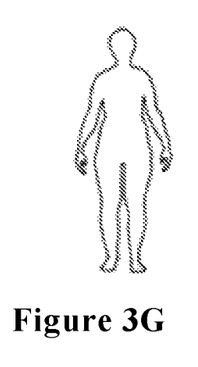
Figure 3H:
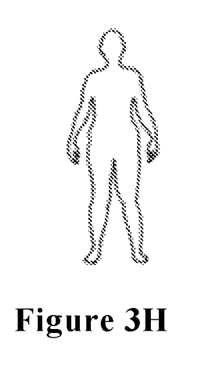
Figure 3I:
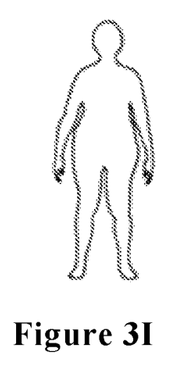

Pear (FIG. 3G)
The classic pear shape does not mean "chubby"; it is about weight distribution, with more weight below the waist than above, and larger thighs and calves.
Skittle (FIG. 3H)
Smaller bottom than the Pear and no "saddlebags" (weight gathered on the outside of the thighs); Skittles are generally taller and thinner but still carry weight around their thighs.
Bell (FIG. 3I)
Small shoulders and small, short waist with a large bottom and thighs.

Group 4 Body Shapes—Everything Else

Figure 3J:
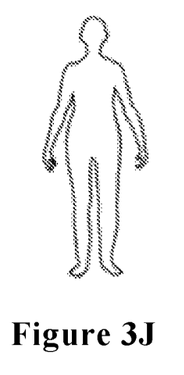
Figure 3K:
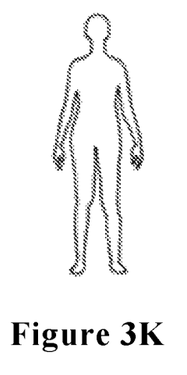
Figure 3L:
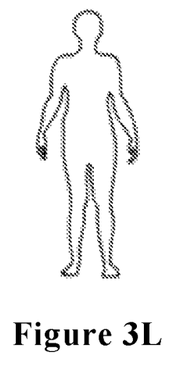

Column (FIG. 3J)
Generally taller, Columns have shoulders the same size as hips, slim waists and long legs.
Lollipop (FIG. 3K)
Generous bosom, long legs, slim waist and hips are the hallmarks of this shape.
Cornet (FIG. 3L)
Boyish and athletic, Cornets have smaller breasts, broad shoulders and longer legs.

Figure 4:
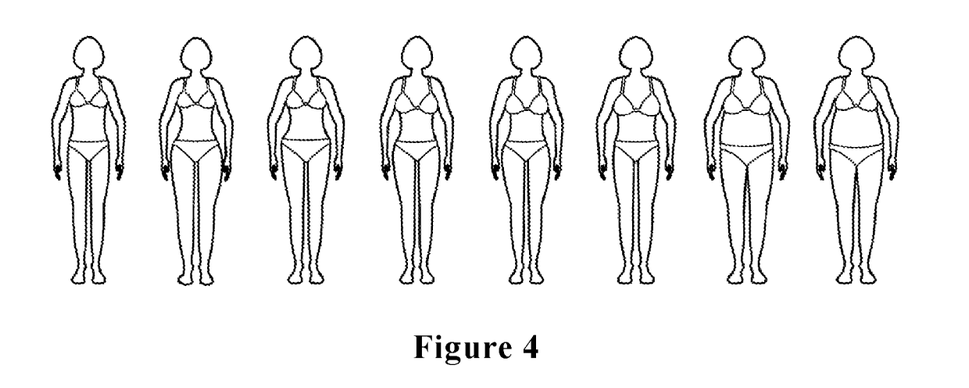
FIG. 4 illustrates the eight body shapes generally defined and used in the art in the US.

In the US, the following eight body shape definitions are commonly used in the art for women. Across FIG. 4 from left to right, these eight shapes are: Straight, Pear, Spoon, Hourglass, Top Hourglass, Inverted Triangle, Oval, and Diamond.

Figure 5A:
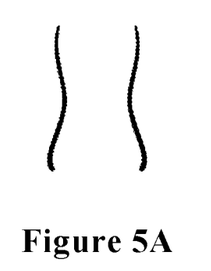
FIGS. 5A to 5H illustrate torso areas of the eight body shapes shown in FIG. 4.

Straight Body Type (FIG. 5A)
The bust and hips are basically the same size. The waist is slightly smaller than the bust and hips. This is the most common body type. Over 45% of American women have a Straight body shape (sometimes called rectangle or ruler body shape).
Hips and bust are balanced
Waist is not very defined
A bottom that is more flat than round
Tend to gain weight in the torso first and then the upper thighs and arms
Lower legs are shapely.

Figure 5B:
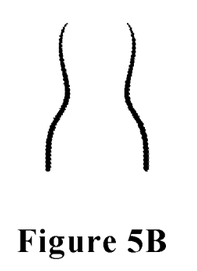

Pear Body Type (FIG. 5B)
The hips are larger than the bust, and the waist gradually slopes out to the hips. Typical characteristics of a Pear shaped body (sometimes called triangle) are:
Hips are larger than the bust
Defined waist
Elegant neck and proportionately slim arms and shoulders
First gain weight in the bottom and legs, followed by tummy and upper body.

Figure 5C:
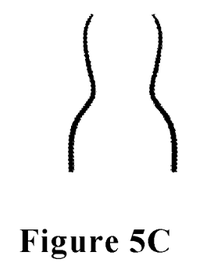

Spoon Body Type (FIG. 5C)
The hips are larger than the bust and the hips have a "shelf" appearance. The waist is slightly smaller than the bust. A Spoon Body type (sometimes called FIG. 8) is quite common. Typical characteristics are:
Hips are larger than the bust
Defined waist
Hips have a "shelf" appearance
Prone to gaining weight in the tummy and a tendency towards "love-handles" (defined as the "pinch-able" fat on both sides of the stomach region).

Figure 5D:
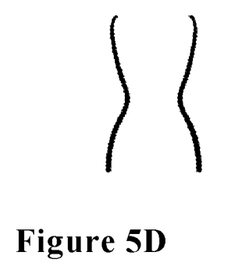

Hourglass Body Type (FIG. 5D)
The bust and hips are approximately the same size and the waist is well defined. The Hourglass body type is the body shape that many women strive for. Typical characteristics are:
Bust and hips are well balanced
Defined waist
Gently rounded shoulders that align nicely with the hips
Waist is obvious and gracefully curves out to the hips
A rounded bottom and side as well as front profile
Upper body is proportionate in length to the legs which are shapely.

Figure 5E:
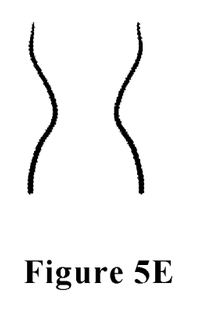

Top Hourglass Body Type (FIG. 5E)
The bust is larger than the hips and the waist is well defined. A top hourglass body type has a defined wait and bust larger than the hips. Gently rounded shoulders align with the hips. Waist is obvious and curves out to the hips. Most likely a rounded bottom and side prominence as well as front profile. Upper body is propionate in tenth to the legs which are shapely.

Figure 5F:
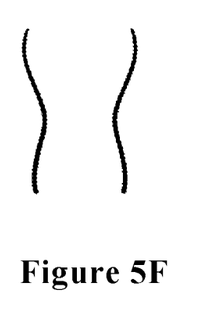

Inverted Triangle Body Type (FIG. 5F)
The bust is large, the hips are narrow and the waist is not very well defined (also known as an athletic body type). Typical characteristics are:

Proportionally larger upper body
Broad shoulders, and ample bust and a wide back
Hips are slim and bottom may have a tendency towards the flat side
Waist is subtle, tendency to gain weight in the belly and upper body
Shapely legs.

Figure 5G:
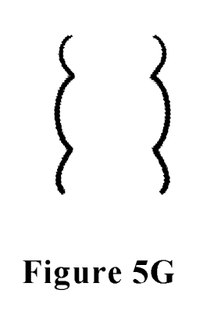

Oval Body Type (FIG. 5G)

The waist is larger than the bust and hips. The hips are narrow compared to the shoulders. Breasts are ample in size. Typical Characteristics of an Oval body type (sometimes known as an apple body shape) are:
Large bust, narrow hips, and a full midsection
Tendency to gain weight in the stomach, back and upper body
Waist is undefined and the widest part of the frame
Shorter neck and full face
Buttocks are somewhat flat and legs are slender.

Figure 5H:
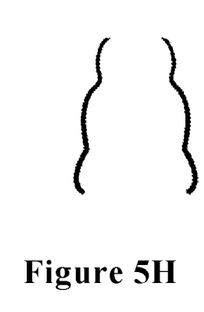

Diamond Body Type (FIG. 5H)

The waist is larger than the bust and hips. The shoulders are narrow compared to the hips. Breasts are small to medium in size. A Diamond body type is uncommon. Typical characteristics are:
Hips are broader than the bust and shoulders
Tendency to gain weight in the stomach, back, hips and buttocks
Waist is undefined and the widest part of the frame
Carry some weight in upper legs
Lower legs are shapely
Proportionately slender, shapely arms.

Endomorph—big, relatively high body fat, often pear-shaped, generally with a high tendency to store body fat.
Mesomorph—muscular and well-built, generally with a high metabolism and responsive muscle cells.

Male Shape (Descriptive)
  Rectangle
  Triangle
  Oval
  Inverted Triangle

Male Shape (Ergonomic)
  Ectomorph—lean and long, generally with difficulty building muscle.
  Endomorph—big, relatively high body fat, often pear-shaped, high tendency to store body fat.
  Mesomorph—muscular and well-built, generally with a high metabolism and responsive muscle cells.

Child
  Pear-Shaped—as above
  Round/Apple—as above
  Diamond—as above
  Triangle—as above
  Inverted Triangle—as above
  Tubular—similar to the "Straight" body type discussed above; the ratios between the volumes of the chest, abdomen and pelvis are broadly equal and do not vary between each other by more than 15%.

Table 1, below, illustrates part volume measurements for four women with four different body shapes.

TABLE 1

| Body Type | | Total Volume | Right Leg Volume | Left Leg Volume | Chest Volume | Left Arm Volume | Right Arm Volume | Pelvis Volume | Abdomen Volume |
|---|---|---|---|---|---|---|---|---|---|
| Athletic | Total Volume (Ltrs) | 59.3 | 7.7 | 7.8 | 21.7 | 2.1 | 2.0 | 8.6 | 9.4 |
| Athletic | Percent (%) | 100.0 | 13 | 13.1 | 36.7 | 3.5 | 3.4 | 14.5 | 15.8 |
| Athletic | Part Volume Ratio | Chest Volume at least 10% more than the combined Pelvis & Abdomen volume. For extreme Athletic build arm volume will be a factor | | | | | | | |
| Hour-glass | Total Volume (Ltrs) | 64.8 | 10 | 10.1 | 20.6 | 2.3 | 2.4 | 10.3 | 9.1 |
| Hour-glass | Percent (%) | 100.0 | 15.4 | 15.5 | 31.7 | 3.7 | 3.7 | 16.0 | 14.0 |
| Hour-glass | Part Volume Ratio | Abdomen Volume at least 10% less than both Pelvis and Chest volume | | | | | | | |
| Pear | Total Volume (Ltrs) | 112.3 | 15.8 | 15.6 | 35.7 | 3.7 | 3.6 | 13.3 | 24.6 |
| Pear | Percent (%) | 100.0 | 14.1 | 13.9 | 31.7 | 3.3 | 3.2 | 11.9 | 21.9 |
| Pear | Part Volume Ratio | The part Volumes of the combined Abdomen and Pelvis larger than the total Chest Volume | | | | | | | |
| Apple | Total Volume (Ltrs) | 93.7 | 10.4 | 10.5 | 33.5 | 3.6 | 3.7 | 16.3 | 15.7 |
| Apple | Percent (%) | 100.0 | 11.1 | 11.2 | 35.8 | 3.8 | 3.9 | 17.4 | 16.8 |
| Apple | Part Volume Ratio | The ratio of the Volume of the Pelvis to the Abdomen Volume approximately equal to one (volumes approximately equal) | | | | | | | |

Other examples of body shape definition lists are provided below, by way of non-limiting example:

Female Shape (Descriptive)
  Hourglass
  Pear-Shaped
  Round/Apple
  Diamond
  Triangle
  Inverted Triangle Female Shape (Ergonomic)
  Ectomorph—lean and long, generally with difficulty building muscle, The ratios used to categorise these four women into the listed body shapes are shown in the table.

The main body part volumes used are chest, abdomen and pelvis.

The main ratios used in this embodiment are:
(chest)/(abdomen+pelvis)
(abdomen)/(pelvis)
(abdomen)/(chest)

Another embodiment using the same main body part volumes may use different ratios or combinations of ratios. The skilled person will appreciate that suitable embodiments may vary depending on age, ethnicity, clothing manufacturer, and/or other variables. One such further embodiment is laid out below.

The main ratios used in this embodiment are:
(chest)/(abdomen+pelvis)
(chest)/(total)

Abdomen and pelvis combined volume is approximately 34%

The total volume of chest, abdomen and pelvis makes up approximately 70% of the total body volume Table 2, below, illustrates part volume measurements for three men with three different body shapes.

TABLE 2

| Body Type | | Total Volume | Right Leg Volume | Left Leg Volume | Chest Volume | Left Arm Volume | Right Arm Volume | Pelvis Volume | Abdomen Volume |
|---|---|---|---|---|---|---|---|---|---|
| Inverted Triangle | Total Volume (Ltrs) | 82.7 | 9.5 | 9.4 | 32.6 | 3.1 | 3.2 | 12.2 | 12.7 |
| Inverted Triangle | Percent (%) | 100.0 | 11.5 | 11.4 | 39.5 | 3.7 | 3.9 | 14.7 | 15.3 |
| Inverted Triangle | Part Volume Ratio | Volume of the Chest more than the Pelvis and Abdomen combined, and the variance between the Pelvis and Abdomen volumes being less than 10% | | | | | | | |
| Rectangle | Total Volume (Ltrs) | 81.7 | 10 | 9.9 | 29.4 | 3.0 | 3.1 | 13.8 | 12.5 |
| Rectangle | Percent (%) | 100.0 | 12.2 | 12.1 | 36.0 | 3.7 | 3.8 | 16.9 | 15.3 |
| Rectangle | Part Volume Ratio | Volume of the Pelvis and the Abdomen comparable to the Volume of the Chest with a variance of less than 15% between each of the three volumes | | | | | | | |
| Oval | Total Volume (Ltrs) | 92.8 | 7.5 | 7.6 | 37.1 | 3.1 | 3.1 | 15.5 | 19.0 |
| Oval | Percent (%) | 100.0 | 8 | 8.2 | 40 | 3.3 | 3.3 | 16.7 | 20.5 |
| Oval | Part Volume Ratio | Volume of the Abdomen higher than the Pelvis Volume | | | | | | | |

(abdomen+pelvis)/(total)
(chest+abdomen+pelvis)/(total)
Athletic
  Chest volume is slightly higher than abdomen and pelvis combined, with little or no waist definition–ratio: (chest)/(abdomen+pelvis)>1
  Chest volume is approximately 35% of total body volume–ratio:(chest)/(total)~0.35
  Abdomen and pelvis combined volume is approximately. 30% of total body volume–ratio:(abdomen+pelvis)/(total)~0.30
  The total volume of chest, abdomen and pelvis makes up approximately 65% of the total body volume–ratio: (chest+abdomen+pelvis)/(total)≈0.65
Hourglass
  Chest volume is equal to pelvis and abdomen volumes combined with strong waist definition–ratio:(chest)/(abdomen+pelvis)≈1
  Chest volume is approximately 30% of total body volume
  Abdomen and pelvis combined is approximately 30% of total body volume
  The total volume of chest, abdomen and pelvis makes up approx. 60% of the total body volume
Pear
  Abdomen and pelvis combined volume is greater than the chest volume.
  The total leg volume is the same as the chest volume–ratio:(left leg+right leg)/(chest)≈1
  Chest volume is approximately 30% of total body volume
  Abdomen and pelvis combined is approximately 34% of total body volume
  The total volume of chest, abdomen and pelvis makes up approximately. 64% of the total body volume
  The legs volume is approximately 30% of the total body volume–ratio:left leg+right leg)/(total)≈0.3
Apple
  Rounded in shape, the chest volume is almost the same as abdomen and pelvis combined.
  Chest volume is approximately 35%

The ratios used to categorise these three men into the listed body shapes are shown in the table. The skilled person will appreciate that, for example, variance between the Pelvis and Abdomen volumes being less than 10% may be thought of as the ratio between the two being 1+/−0.10.

The main body part volumes used are chest, abdomen and pelvis, as for the women.

The main ratios used in this embodiment are:
(chest)/(abdomen+pelvis)
(abdomen)/(pelvis)

Another embodiment using the same main body part volumes may use different ratios or combinations of ratios. One such embodiment is laid out below.

The main ratios used in this embodiment are the same as for women:
(chest)/(abdomen+pelvis)
(chest)/(total)
(abdomen+pelvis)/(total)
(chest+abdomen+pelvis)/(total)
Inverted Triangle
  The chest volume is greater than the abdomen and pelvis combined.
  Chest volume is approximately 38% of total body volume
  Abdomen and pelvis combined is approximately 30% of total body volume
Rectangle
  The volume of the abdomen and pelvis combined is approximately the same as the volume of the chest with little or no waist definition
  Chest volume is approximately 34%
  Abdomen and pelvis combined is approximately 32%
Oval
  Most weight centred on chest, abdomen and pelvis with chest being approximately the same volume as abdomen and pelvis combined.
  Chest volume is approximately 39% of body volume
  Abdomen and pelvis combined is approximately 37% of body volume
  The chest, abdomen and pelvis combined is approximately 76% of the total body volume Triangle
- The chest has a lower volume than the abdomen and pelvis combined
- Excess volume also in the legs–ratio:(left leg+right leg)/(total)

The skilled person will appreciate that these examples of lists of body shapes are not limiting. For example, any given clothing manufacturer or retailer may provide their own definitions, a subset of either of the above lists could be used, or a different list could be used.

Figure 6:
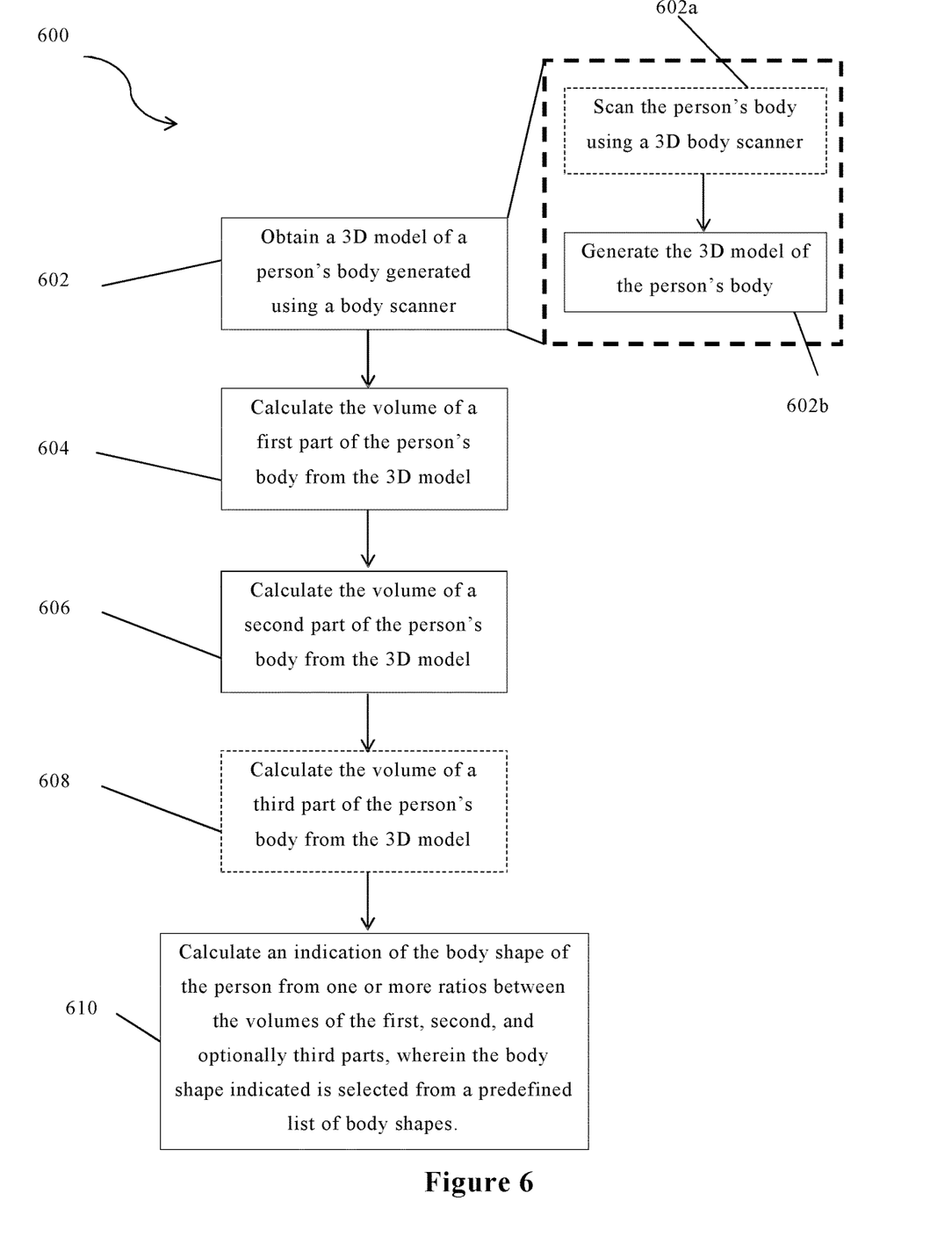
FIG. 6 shows a flow chart of a method of an embodiment.

FIG. 6 illustrates a method 600 of an embodiment of the invention.

At step 602, a 3D model of a person's body is obtained.

The 3D model is generated using a scanner—as used herein, a "body scanner" or scanner is any device and/or software which can be used to create a three-dimensional model of a person. The steps of scanning 602a the person's body using the 3D scanner and generating 602b the 3D model based on the scan data may be performed as part of the method 600, or may be performed at an earlier time, optionally using a different device. The scanning step 602a may be replaced or supplemented with receiving data from another source in some embodiments; for example, a 3D model may be generated by "body scanner" software on the basis of a plurality of 2D images provided to the software.

The obtaining step 602 may instead comprise downloading and/or opening 3D model data generated previously.

At step 604, the volume of a first part of the person's body is calculated from the 3D model.

At step 606, the volume of a second part of the person's body is calculated from the 3D model.

The first and second parts may be two parts of the person's torso; e.g. chest and abdomen, pelvis and abdomen, pelvis and chest, or torso below waist level and torso above waist level.

At optional step 608, the volume of a third part of the person's body is calculated from the 3D model. The third part may be a total body volume.

The skilled person will appreciate that the method steps may be performed in a different order. For example, the part volumes may be calculated in advance and provided with the 3D model.

At step 610, an indication of the body shape of the person is calculated from one or more ratios between the volumes of the first, second and/or third parts. Optionally, a plurality of ratios may be used. Optionally, three or more part volumes can be combined into a single ratio, for example (chest+pelvis):(abdomen).

The body shape indicated is selected from a predefined list. The method may further comprise inputting a selection of a predefined list from a plurality of predefined lists, or inputting data to allow a predefined list to be selected automatically.

The invention claimed is:

1. A body shape indicator device comprising:
a body volume calculator for calculating amounts of space taken up by respective body parts, the body volume calculator being arranged to:
  receive a three-dimensional (3D) model of a person generated using a scanner; and
  calculate the volume of at least a first, a second, and a third par of the person's body from the 3D model, the first, second and third parts being chest, pelvis and abdomen, each volume being a measure of the amount of space taken up by the respective part of the person's body in 3 dimensions; and a body shape calculator arranged to calculate an indication of the person's body shape based on one or more ratios between volumes of the first, second, and third parts, wherein the body shape indication is an indication of a body type selected from a predefined list of body shapes.

2. The body shape indicator device of claim 1, wherein the body volume calculator is arranged to calculate the volume of a fourth part of the person's body from the 3D model; and
the body shape calculator is arranged to calculate the indication of the person's body shape based on one or more ratios between volumes of the first, second, third and/or fourth parts.

3. The body shape indicator device of claim 2, wherein the fourth part is total body volume.

4. The body shape indicator device of claim 1 or claim 2, further comprising:
the scanner arranged to obtain scan data and generate the 3D model of the person from the scan data.

5. A body shape indicator device according to claim 1, wherein the body volume calculator is arranged to calculate the volume of a further part chosen from:
torso below the waist and torso above the waist.

6. A body shape indicator device according to claim 1, in which the body volume calculator is arranged to calculate the volume of further predetermined parts of the person's body, which are used by the body shape calculator to calculate the indication of the person's body shape.

7. A body shape indicator device according to claim 1, in which the device is arranged to associate the first, second, third, and any further predetermined parts with an importance factor, which is used to give more importance to particular parts of the body in the calculation of the indication of the person's body shape.

8. A body shape indicator device according to claim 1, in which the device is arranged to calculate the volume of a total of seven body parts, the seven body parts being left arm, right arm, left leg, right leg, chest, abdomen, and pelvis.

9. A body shape indicator device according to claim 1, in which the body volume calculator is arranged to manipulate the data output from the scanner using triple integration.

10. A body shape indicator device according to claim 1, in which the body shape indicator device is additionally arranged to calculate linear measurements from the 3D model and to provide an indication of a suitable clothing sizing fit based at least in part on the body shape indication and the linear measurements of the person.

11. A body shape indicator device according to claim 1, in which the body shape indicator device is additionally arranged to provide a graphic code encoding at least one of the indication of the person's body shape and measurements of the person.

12. A body shape indicator device according to claim 11, in which the graphic code is a QR code.

13. A method for determining the body shape of a person comprising the steps of:
obtaining a three-dimensional (3D) model of the person's body generated using a scanner;
calculating the volume of a first part of the person's body from the 3D model, the calculated volume being a measure of the amount of space taken up by the first part of the person's body, wherein the first part is the chest;
calculating the volume of a second part of the person's body from the 3D model, the calculated volume being a measure of the amount of space taken up by the second part of the person's body in three dimensions, wherein the second part is the pelvis;

calculating the volume of a third part of the person's body from the 3D model, the calculated volume being a measure of the amount of space taken up by the third part of the person's body in three dimensions, wherein the third part is the abdomen; and calculating an indication of the body shape of the person from one or more ratios between the volumes of the first, second and third parts, wherein the body shape indication is an indication of a body type selected from a predefined list of body shapes.

14. The method of claim 13, further comprising at least one of:
   (i) scanning the person's body, optionally using the scanner; and
   (ii) generating the 3D model of the person's body, using the scanner.

15. The method of claim 13, further comprising providing a graphic code arranged to encode or provide access to the body shape indication.

16. The method according to claim 15, in which the graphic code is a QR code.

17. A machine readable medium containing instructions which when read by a machine cause that machine to perform as the body shape indicator device of claim 1.

* * * * *

UNITED STATES PATENT AND TRADEMARK OFFICE
CERTIFICATE OF CORRECTION

| | | |
|---|---|---|
| PATENT NO. | : 11,798,186 B2 | Page 1 of 1 |
| APPLICATION NO. | : 17/042660 | |
| DATED | : October 24, 2023 | |
| INVENTOR(S) | : Barnes | |

It is certified that error appears in the above-identified patent and that said Letters Patent is hereby corrected as shown below:

In the Claims

Column 21, Line 63, Claim 1:
Delete "par" and insert --part--.

Signed and Sealed this
Twelfth Day of December, 2023

Katherine Kelly Vidal
*Director of the United States Patent and Trademark Office*